United States Patent
Robert

(10) Patent No.: US 6,511,490 B2
(45) Date of Patent: Jan. 28, 2003

(54) GASTRIC BANDING DEVICE AND METHOD

(76) Inventor: Antoine Jean Henri Robert, Rua Joana Angelica, 134 Apt 601, Ipanema, Rio de Jeneiro (22420-030) (BR)

( * ) Notice: Subject to any disclaimer, the term of this patent is extended or adjusted under 35 U.S.C. 154(b) by 22 days.

(21) Appl. No.: 09/887,996

(22) Filed: Jun. 22, 2001

(65) Prior Publication Data

US 2002/0198548 A1 Dec. 26, 2002

(51) Int. Cl.$^7$ ............................................. A61B 17/00
(52) U.S. Cl. ....................................................... 606/151
(58) Field of Search ................................ 606/151, 157, 606/158, 213, 217, 139, 140, 142, 153

(56) References Cited

U.S. PATENT DOCUMENTS

| | | | | |
|---|---|---|---|---|
| 3,730,186 A | * | 5/1973 | Edmunds et al. | 128/DIG. 25 |
| 4,592,339 A | * | 6/1986 | Kuzmak et al. | 128/899 |
| 5,074,868 A | * | 12/1991 | Kuzmak | 604/909 |
| 5,160,338 A | * | 11/1992 | Vincent | 600/3 |
| 5,449,368 A | * | 9/1995 | Kuzmak | 604/909 |
| 5,549,621 A | * | 8/1996 | Bessler et al. | 227/902 |
| 5,771,903 A | * | 6/1998 | Jakobsson | 128/897 |
| 6,102,922 A | * | 8/2000 | Jakobsson et al. | 606/157 |

* cited by examiner

*Primary Examiner*—Danny Worrell
(74) *Attorney, Agent, or Firm*—Michael G. Petit

(57) ABSTRACT

A gastric banding device for implantation within a person for the treatment of morbid obesity. The gastric banding device includes an inflatable band portion dimensioned to encircle the stomach and an inflation conduit operable for conducting a percutaneously injected inflation fluid into the band portion. The band portion is a toroidal member having a head end with first fastening means thereon and a tail end having second fastening means thereon and an inflatable shell therebetween. The outer surface of the toroidal shell in reinforced with a non-extensible, biocompatible material which serves to limit outward expansion of the shell when an inflation fluid is injected thereinto. The inner, stomach-contacting surface of the shell has a layer of an open-cell elastomeric foam affixed thereto and integral therewith. In operation, when the band is placed in an encircling relationship with the stomach, the first and second fastening means on the ends of the shell are engaged in locking relationship. An inflation fluid is injected into the shell by means of a subcutaneously implanted injection port that is in fluid communication with the inflation conduit. As the shell expands inwardly, it constricts and compartmentalizes the stomach. The rough textured, open-cell, stomach-contacting layer on the interior surface of the shell prevents post-implantation migration of the shell. The open-cell layer obviates the need for suturing the stomach to prevent slippage of the banding device.

5 Claims, 3 Drawing Sheets

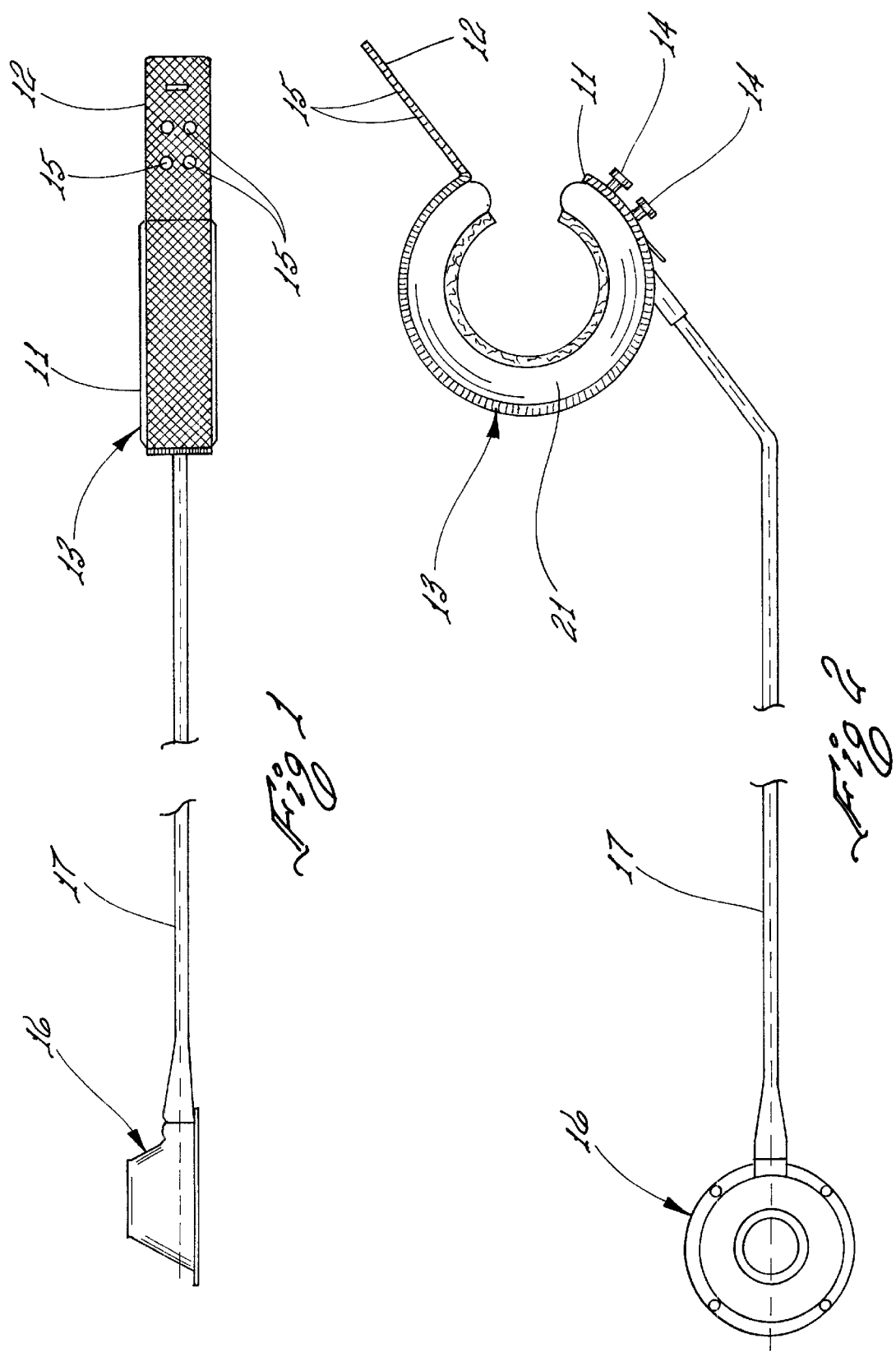

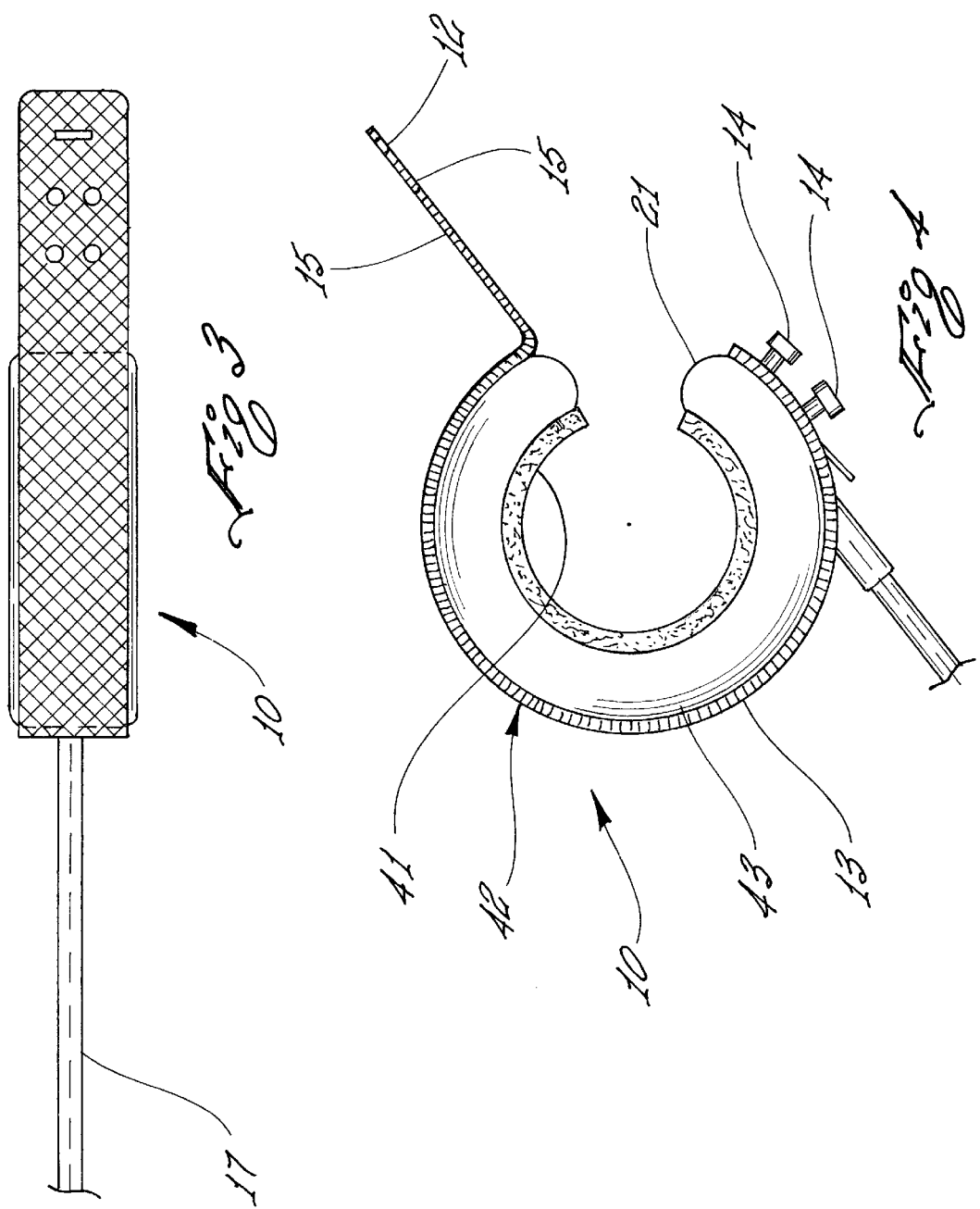

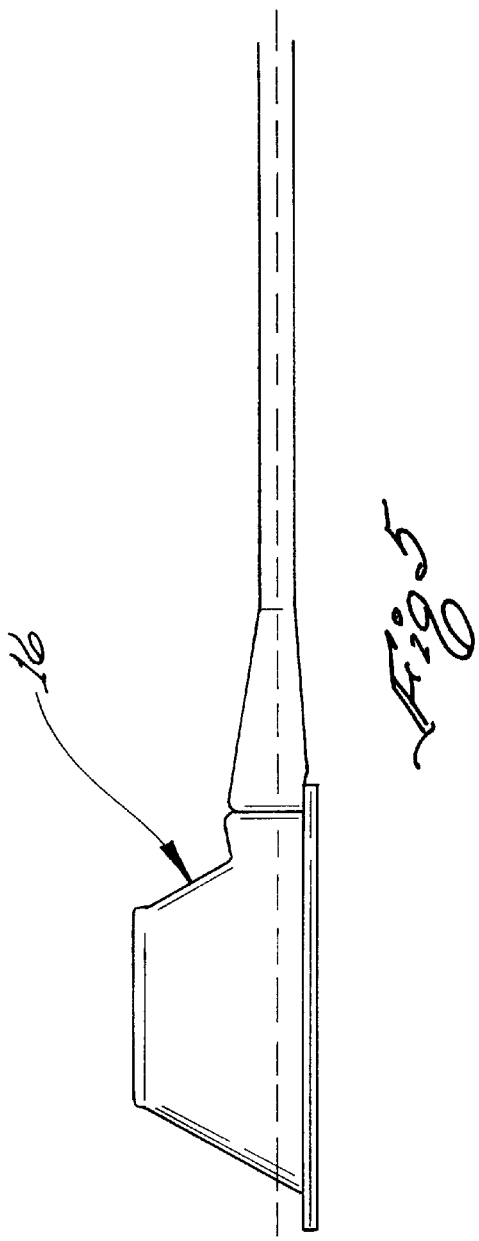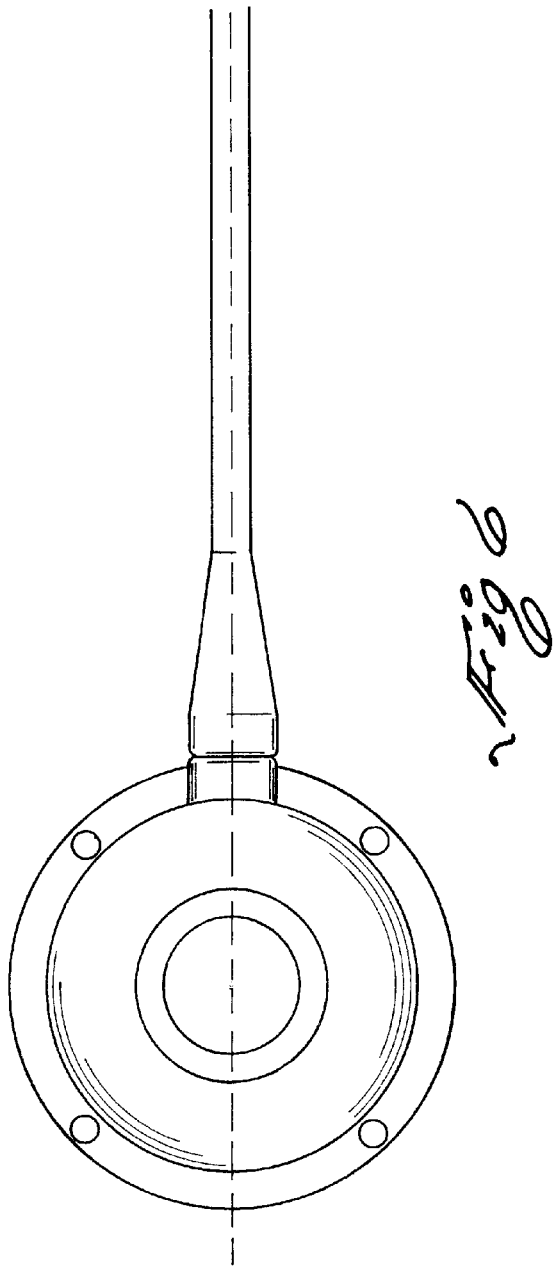
Fig. 5
Fig. 6

GASTRIC BANDING DEVICE AND METHOD

BACKGROUND OF THE INVENTION

1. Field of the Invention

The present invention relates in general to a gastric band for treatment of morbid obesity and more particularly to a gastric band having a rough textured stomach-contacting surface.

2. Prior Art

A current method for treating morbid obesity comprises the placement of a band around a portion of the stomach, either laparoscopically or by open surgery, thereby compressing the stomach and creating a stoma that is less than the normal interior diameter of the stomach. The constricted stoma restricts food intake into the lower digestive portion of the stomach. An exemplary gastric banding device used in this method is disclosed by Kuzmak et al. in U.S. Pat. No. 4,592,339. In its simplest form the gastric band comprises a substantially nonextensible belt-like strap which constrictively encircles the outside of the stomach thereby producing a new stoma and preventing it from expanding. Kuzmak et al also describe a band which includes a balloon-like section that is expandable and deflatable by injection or removal of fluid from the balloon through a remote injection site. The balloon-like expandable section is used to adjust the size of the stoma both intraoperatively and postoperatively.

Although the banding procedure has great promise due to its simplicity and the fact that it retains the desired diameter of the stoma, it is necessary to establish a proper stoma size. To overcome this problem, Kuzmak in U.S. Pat. No. 4,696,288, describes a stoma size calibrating apparatus and method for using the apparatus with a gastric banding device. The calibrating apparatus facilitates controlling the size of the stoma with the gastric band.

In accordance with current practice, the prior art gastric band is operatively placed to encircle the stomach. Once positioned around the stomach, the ends of the gastric band are fastened to one another and the band is held securely in place by folding a portion of the gastric wall over the band and closing the folded tissue with sutures placed therethrough thereby preventing the band from slipping and the encircled stoma from expanding. Most prior art gastric bands that are currently used include a flexible substantially non-extensible band portion having an expandable, balloon-like straight or toroidal shell that is in fluid communication with a remote injection site. Injection or removal of an inflation fluid into or from the interior of the expandable shell is used to adjust the size of the stoma either during or following implantation.

A problem with prior art gastric bands is the aforesaid necessity for folding and suturing the stomach around the shell portion of the band to prevent it from slipping. The shell of prior art gastric bands has a smooth inner stomach-contacting surface which exerts pressure uniformly against the stomach tissue thereby reducing or preventing necrosis which can occur when tissue is pinched as, for example, by a dimpled inner surface on the expanded shell. It would be an advance in the art to provide a gastric banding device that resists slippage following implantation without requiring the placement of sutures in the stomach.

SUMMARY

It is an object of this invention to provide a gastric band adapted for placement in an encircling position around the stomach thereby constricting the stomach and producing a stoma within the band-encircling portion of the stomach which may be adjusted by the percutaneous injection of an inflation fluid into the gastric band via an injection reservoir which is in fluid communication with the gastric band.

It is a further object of the invention to provide a gastric band meeting the above objective and wherein the gastric band is adapted to resist slipping following implantation without the use of sutures to hold the gastric band in position.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE DRAWINGS

FIG. 1 is a side elevational view of a stoma-adjustable gastric band in accordance with the present invention.

FIG. 2 is a top view of the stoma-adjustable gastric band illustrated in FIG. 1.

FIG. 3 is an enlarged side view of the portion of the gastric band device of

FIGS. 1 and 2 that includes an inflatable band.

FIG. 4 is an enlarged top view of the portion of the gastric band device of FIGS. 3 that illustrates the textured elastomeric foam layer on the inner stomach-facing surface of the inflatable band.

FIG. 5 is a side elevational view of an implantable self-sealing injection reservoir adapted for the transcutaneous injection and removal of an inflation fluid into the inflatable portion of the stoma-adjustable gastric band in accordance with the present invention.

FIG. 6 is a top view of the self-sealing injection reservoir of FIG. 5.

DESCRIPTION OF THE PREFERRED EMBODIMENTS

A stoma adjustable gastric band, generally indicated at numeral 10 in FIG. 1, has a buckle end 11, a tail end 12 and a body portion 13 therebetween. The buckle end 11 has a plurality of expanded head projections 14 (visible in FIG. 2) thereon adapted to matingly engage holes 15 in the tail end 12 of the gastric band 10. In practice, the body portion 13 of the gastric band 10 is placed in an encircling position around the stomach to create a pouch adjacent to the esophagus. The expanded head projections 14 are inserted through the holes 15 in the tail end 12 to loosely engage the body portion 13 of the gastric band 10 in an encircling position around the stomach. A stoma-sensing device is introduced transesophageally into the stomach to provide means for measuring the size of the stoma within the stomach. An inflatable balloon 21 affixed to the interior curvature of the body portion of the band is in fluid communication with a remote injection reservoir 16, shown in enlarged detail in FIGS. 5 and 6, by means of a fill tube 17. The surgeon implants the injection port 16 at a suitable location, usually within the rectus sheaths, for transcutaneous access via a hypodermic needle. Postoperative adjustment of the stoma is accomplished by addition or removal of fluid from the balloon 21 by means of a syringe and the hypodermic needle (not shown) percutaneously introduced into the injection port 16.

In accordance with the currently practiced procedure for implanting prior art gastric bands, which are similar in general operation to the gastric band 10 of the present invention, the body portion of the gastric band is then secured about the stomach by appropriate securing means such as a buckling mechanism or by placing sutures through overlapping sections of the band's body portion 13 through a suture hole. The fastened gastric band is then secured in position around a specific portion of the stomach by folding a portion of the encircled stomach over the gastric band and placing one or more sutures in the stomach in order to prevent the prior art gastric bands from slipping. The gastric band is inflated until the correct stoma size is achieved and the stoma-sensing device is then removed from the stomach by the anesthesiologist. Alternatively, a radiopaque fluid may be introduced into the stomach and the stoma viewed by radiographic visualizing means during the inflation procedure.

The construction of prior art gastric bands require the aforementioned traumatic step of suturing the band to the stomach. Even when a portion of the stomach is folded over a section of the body portion of the gastric band and sutured, there remains a tendency for other segments of the gastric band that are not enveloped by the stomach to slip. In addition, there is a possibility of tissue erosion on the portion of the stomach wall encircled by the prior art gastric bands. The gastric band 10 of the present invention is designed to overcome these problems. Turning now to FIG. 4, the body portion of the gastric band 10 of the present invention is shown in greater detail. Unlike prior art gastric banding devices, the stoma-adjustable gastric band 10 has a layer of rough textured elastomeric foam 41 affixed to the inner stomach-facing surface of the body portion 13 of the gastric band 10. The rough textured elastomeric foam layer 41 may be formed of any biocompatible material but is preferably either open-cell polyurethane or silicone foam.

With continuing reference to FIG. 4, the body portion 13 of the gastric band 10 includes an inflatable balloon 21 that is formed by repetitively dipping a curved mandrel into a dispersion of uncured silicone elastomer. A strip of uncured Dacron®-reinforced silicone having expanded head posts 14 and holes 15 thereon is vulcanized to the outer surface of the inflatable balloon to provide an non-extensible outer retaining strap 42. A strip of partially cured silicone elastomer 43 is interposed between the layer of elastomeric foam 41 and the inflatable balloon and compressed until portions of the partially cured elastomeric strip extrude into open cells on the surface of the foam layer. The fill tube 17 is attached to the inflatable balloon such that the central lumen of the fill tube is in fluid communication with the interior of the inflatable balloon and the assembly vulcanized to form an integral body portion 13.

As mentioned above, with prior art gastric banding devices, erosion of the gastric wall can occur due to relative movement between the prior art gastric band and the underlying wall of the stomach following implantation of the band. The interposition of a rough-textured, biocompatible elastomeric surface of a compressible foam between the inflatable balloon and the gastric wall provides means for reducing relative motion between the present gastric band and the stomach wall thereby reducing the incidence of tissue erosion. In addition, the presence of a rough-textured stomach contacting surface on the gastric band serves to resist slippage and repositioning of the gastric band following implantation.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A gastric banding device operable for placement in an encircling position around a stomach, thereafter to be adjusted to constrict a portion of the stomach encircled by the gastric banding device, said gastric banding device comprising a rough-textured foam layer on an inner stomach-contacting surface thereof.

2. The gastric banding device of claim 1 wherein said rough-textured foam layer comprises an open cell elastomer.

3. The gastric banding device of claim 2 wherein said elastomer is polyurethane.

4. The gastric banding device of claim 2 wherein said elastomer is silicone.

5. The gastric banding device of claim 1 wherein said gaid gastric banding device includes a body portion adapted to be placed in an encircling relationship around a portion of the stomach, an injection port adapted to be implanted beneath the skin and a fill tube providing fluid communication between said injection port and an inflatable balloon comprising said body portion.

* * * * *